United States Patent [19]

Brown et al.

[11] Patent Number: 5,243,929
[45] Date of Patent: Sep. 14, 1993

[54] TUBULAR SANITARY SIGHT INDICATOR

[75] Inventors: David E. Brown, Brunswick; David E. Purcel, Elyria, both of Ohio

[73] Assignee: Clark-Reliance Corporation, Strongsville, Ohio

[21] Appl. No.: 764,837

[22] Filed: Sep. 24, 1991

[51] Int. Cl.$^5$ .................... G01L 23/06; G02B 7/00
[52] U.S. Cl. .................... 116/276; 277/169; 359/894; 422/55
[58] Field of Search ............... 116/276; 359/894, 513; 73/331; 422/55; 277/169, 207 A

[56] References Cited

U.S. PATENT DOCUMENTS

| | | | |
|---|---|---|---|
| 2,503,033 | 4/1950 | Engelmann | 73/326 X |
| 2,681,034 | 6/1954 | Mannion | 116/276 |
| 2,789,844 | 4/1957 | Kessler | 277/169 X |
| 2,817,309 | 12/1957 | Wittlin | 116/276 |
| 3,185,128 | 5/1965 | Moore et al. | |
| 3,340,890 | 9/1967 | Raskhodoff | 359/894 |
| 3,380,303 | 4/1968 | Le Roy | 359/894 X |
| 4,064,826 | 12/1977 | Pauli | 359/894 X |
| 4,441,365 | 4/1984 | Schulz et al. | 359/894 X |
| 4,961,628 | 10/1990 | Herberts | |

OTHER PUBLICATIONS

"Ferrule Plate-PMH Air Pilot Float Control" Majonnier Bros. Co., 1 sheet, Apr. 7, 1978.
Metaglas brochure, Herberts Ubdystruegkas GmbH & Co. KG (4 pages).
"The Source" Clark-Reliance brochure, 1991, (4 pages).
Sight Flow Indicators by Jacoby-Tarbox, Clark Reliance brochure, 1990.
E-3-A Sanitary Standards for Fittings Used on Egg and Egg Products Equipment and Used on Sanitary Lines Conducting Egg and Egg Products, No. E-0800, Nov. 1971, Journal of Milk and Food Technology, vol. 34, No. 11, pp. 1-30.
Tentative Revisions of the 3-A Sanitary Standards for Fittings Used on Milk and Milk Products Equipment, No. T-08-21 Rev., Feb. 1991, pp. 1-9.
3-A Sanitary Standard for Sight and/or Light Windows..., T-08-22, Aug. 1991, 6 pages.
3-A Sanitary Standards for Flow Meters for Milk and Milk Products, No. 28-01 Dairy and Food Sanitation, Sep. 1988, pp.498-499.
E-3-A Sanitary Standards for Flow Meters for Liquid Egg Products, No. E-2800, pp. 457-459 (May 1979).
Part 2 of the 3-A Sanitary Standards for Fittings Used on Milk and Milk Products Equipment..., No. 08-17 Rev., formulated by Int. Assoc. of Milk, Food & Environmental Sanitarians, US Public Health Service.

Primary Examiner—Daniel M. Yasich
Attorney, Agent, or Firm—Calfee, Halter & Griswold

[57] ABSTRACT

A sanitary sight indicator for viewing the contents of a production process is provided. The sanitary sight indicator includes a body, an optical unit, and a sanitary connection between the body and the optical unit. The body includes a process-interfacing portion which is adapted to interface with the production process and an optical-interfacing portion which interfaces with the optical unit. The optical unit includes a viewing portion for viewing the contents of the production process and a body-interfacing portion which interfaces with the optical-interfacing portion of the body. The sanitary connection includes a sanitary gasket having a substantially flat annular portion, and first and second annular projections which are approximately semi-circular in cross-sectional shape and which extend outwardly from opposite sides of the annular portion. The sanitary connection further includes a sanitary gasket-groove in each of the optical unit-interfacing portion and the body-interfacing portion. Each of the sanitary-gasket grooves includes a flat surface supporting the flat annular portion of the sanitary gasket and a channel supporting one of the annular projections of the sanitary gasket. Such a sight indicator may be in the form of a "sight flow indicator" for installation in a process line or a "sight window" for installation on a process tank.

16 Claims, 4 Drawing Sheets

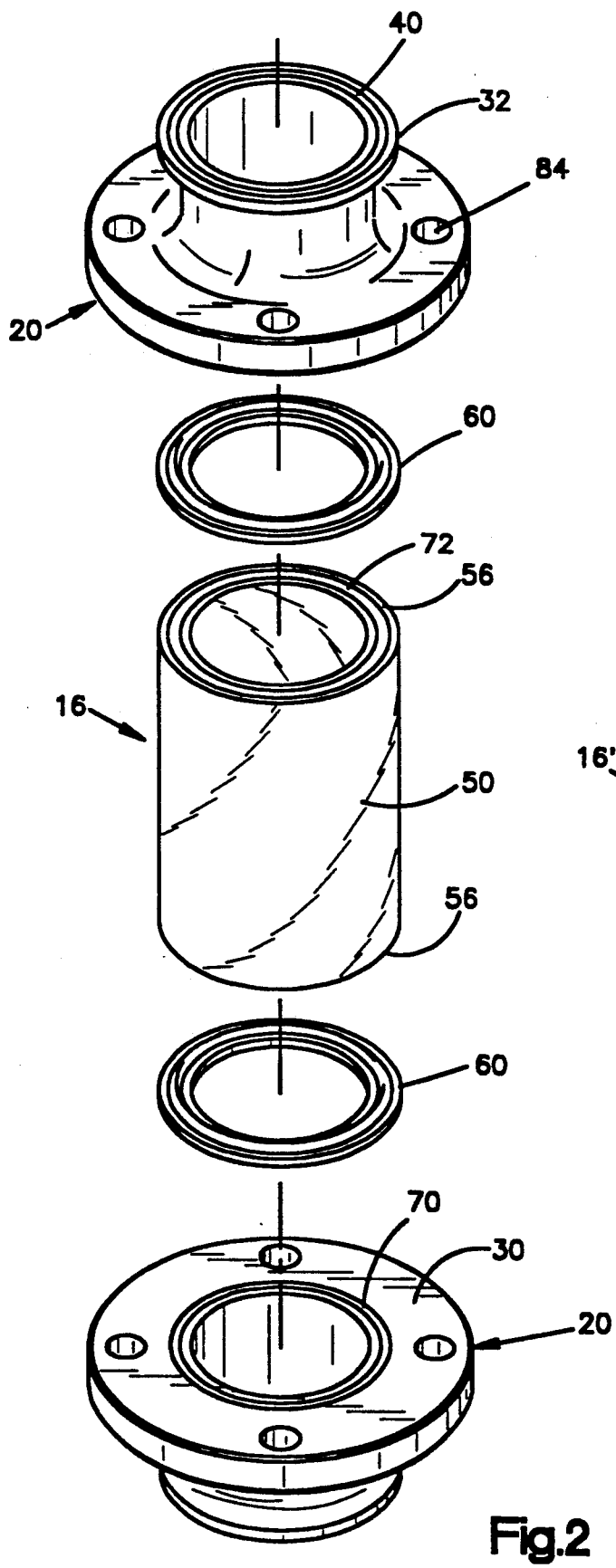
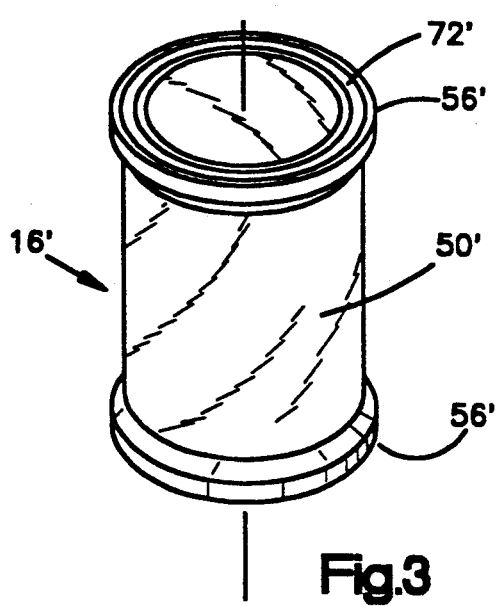
Fig.2
Fig.3

TUBULAR SANITARY SIGHT INDICATOR

FIELD OF THE INVENTION

This invention relates generally as indicated to a sanitary sight indicator and more particularly to a sight indicator in which a sanitary connection is made between the body and the optical unit of the indicator.

BACKGROUND AND SUMMARY OF THE INVENTION

A typical production process will include the flow of a fluid-like substance through process lines and/or the storing of a substance within process tanks. Sight indicators are commonly installed in such process lines and process tanks for the observation of the contents of the production process. This observation may be accomplished by visual inspections performed by personnel, measurement data gathered by instrumentation, or a combination of both.

A sight indicator will usually be in the form of either a "sight flow indicator" installed in a process line to observe the relevant characteristics of the contents flowing therethrough or a "sight window" installed on a process tank to observe the pertinent parameters of the contents stored therein. These characteristics/parameters may include color, clarity, degree of mixing, liquefaction, formation of voids or bubbles, turbidity, light refraction, and effectiveness of cleaning solutions. With particular reference to a sight window, it is commonly also used to determine significant height dimensions, such as the overall level of the contents stored in the process tank or the location of interfaces between the components of multi-component mixture (e.g. the interface between oil and water in an oil/water mixture or the interface between solids and liquids in a multiphase mixture).

A sight indicator will usually include a body, an optical unit, and a connection between the body and the optical unit. The body typically includes a process-interfacing portion which is adapted to interface with the production process and an optical unit-interfacing portion which interfaces with the optical unit, via the connection between these components. The optical unit typically includes a viewing portion for viewing the contents of the production process and a body-interfacing portion which interfaces with the optical unit-interfacing portion of the body.

In many industries, such as those concerned with the production of food, pharmaceutical and/or cosmetic products, sanitation requirements impose certain restrictions on the design of sight indicators. These sanitation requirements include the necessity that leakage into the production process be kept at an extreme minimum to eliminate even the possibility of contamination. Such leakage has commonly been discovered in the connection between the body and the optical unit of sight indicators.

Additionally, such sight indicators must usually be designed so that the opportunity for the contents of the production process to become lodged in the components and/or the crevices between the components of the sight indicator is minimized to industry-accepted levels. This design criteria is necessary because lodged particles typically result in the formation of bacteria which could also result in contamination of the contents of the production process. In the past, the connection between the body and the optical unit has been viewed as a prime candidate for such content lodging.

Still further, industries involved in the production of food, pharmaceutical and/or cosmetic products tend to shy away from sight indicators in which there is a tendency towards failure of the components. This tendency is due to the fact that the failure of certain components, such as a glass viewing portion, may result in fragments being introduced into the production process thereby contaminating its contents. Thus the optical unit, as well as the connection between the optical unit and the body, must be designed to minimize the possibility of such failure. Consequently, industries typically demand that sight indicators be tested at pressure which is at least 1.5 times greater than the maximum working pressure of the production process. For example, in a production process having a maximum working pressure of 150 psig (which is typical of most relevant industries), the test pressure of a sight indicator would have to be at least 225 psig.

The spirit of these restrictions, especially those concerned with leakage and lodging, are reflected in industry requirements that components incorporated into a sanitary production process, such as valves, diaphragms etc., interface with the production process in such manner that the interface qualifies as a "sanitary fitting" or "sanitary connection." "Sanitary connection" in this context corresponds to a connection which satisfies generally accepted and approved industry standards, such as those formulated by the International Association of Milk, Food, and Environmental Sanitarians, the United States Department of Agriculture, the Poultry & Egg Institute of America, the Dairy and Food Industries Supply Association, the Dairy Industry Committee, the United States Public Health Service, and/or other organizations addressing similar concerns.

A sanitary connection in a production process is commonly accomplished by either integral connections or connections comprising sanitary clamping, butt-welds or beveled seat fittings. In sanitary clamping connections, sanitary gaskets and corresponding sanitary-gasket grooves are used to form a sanitary connection between the components of the production process. Sanitary gaskets include a substantially flat annular portion and annular projections which are approximately semi-circular in cross-sectional shape and which extend outwardly from opposite surfaces of the flat annular portion.

In contrast to sanitary gaskets, conventional "non-sanitary" gaskets usually consist either of an annular portion which is entirely flat (a "flat" gasket) or an annular portion which is circular in cross section (an "O-ring ring" gasket). These types of gaskets are usually not acceptable for applications requiring a sanitary connection because they cannot satisfy the necessary sanitary standards. More particularly, when a flat gasket is sandwiched between components of a production process, it has a tendency to undesirably "breath in and out" thereby increasing the chances of leakage, content lodging, and/or contamination. Regarding the 0-ring gasket, it, almost by definition, creates a crevice between the sandwiching components in which the contents of the production process may become lodged.

In a typical sanitary connection, a sanitary gasket is sandwiched between two connecting portions each of which contain a sanitary-gasket groove. Such sanitary-gasket grooves are especially designed to accommodate a sanitary gasket. More particularly, a sanitary-gasket groove will include a flat surface for supporting the flat annular portion of the stationary gasket and a channel for supporting the projecting portion of the stationary gasket. Thus when a sanitary gasket is properly sandwiched between two sanitary-gasket grooves, the gasket is firmly held in position (i.e. it will not "breathe in and out") and no crevices are created between the sandwiching components.

According to the present invention, a sanitary sight indicator is provided which includes a sanitary connection between the components of the indicator, namely the body and the optical unit. In this manner, leakage into the production process is kept at an extreme minimum and the contents of the production process will not become lodged in the connection between the body and the optical unit. Additionally, the viewing portion of the optical unit is designed to greatly reduce any tendencies towards failure. In fact, in tests performed on certain prototypes, the indicators demonstrated pressure ratings substantially exceeding 225 psig and thus they could be incorporated into production process having a 150 psig maximum working pressure.

More particularly, the present invention provides a sanitary sight indicator for viewing the contents of a production process. The sanitary sight indicator includes a body, an optical unit, and a sanitary connection between the body and the optical unit. The body includes a process-interfacing portion which is adapted to interface with the production process and an optical-interfacing portion which interfaces with the optical unit. The optical unit includes a viewing portion for viewing the contents of the production process and a body-interfacing portion which interfaces with the optical-interfacing portion of the body. The sanitary connection includes a sanitary gasket having a substantially flat annular portion, and first and second annular projections which are approximately semi-circular in cross-sectional shape and which extend outwardly from opposite sides of the annular portion. The sanitary connection further includes a sanitary gasket-groove in each of the optical unit-interfacing portion and the body-interfacing portion. The sanitary-gasket grooves each include a flat surface supporting the flat annular portion of the sanitary gasket and a channel supporting one of its annular projections.

According to one embodiment of the present invention, the body comprises a pair of head members which are essentially identical and which each include a process-interfacing interfacing portion and an optical unit-interfacing portion. The optical unit is made of a rigid transparent material such as borosilicate glass, acrylic or polycarbonate and it includes a cylindrical viewing portion having two body-interfacing portions on opposite ends thereof. The body-interfacing portions may be substantially co-planar extensions of the cylindrical viewing portion, or alternatively these portions may comprise flanged end portions which are integrally molded with the viewing portion Such a sanitary sight indicator could be incorporated into a production process line as sight flow indicator.

According to other embodiments of the present invention, a window assembly which is disclosed in U.S. Pat. No. 4,961,628 to Herberts is modified and incorporated into a sight indicator as the optical unit. More particularly, the Herberts window assembly is modified so that a sanitary connection may be created between the window assembly, or the optical unit, and the body of the sight indicator. The owner of the Herberts patent is currently obligated to deliver manufactured window assemblies for distribution in the United States, Canada, and Mexico exclusively to the assignee of the present application.

According to one embodiment of the present invention incorporating the Herberts window assembly, the sanitary sight indicator comprises a cross member including two aligned through-flow sections and two aligned transverse sections. The through-flow sections contain the process-interfacing portions and the transverse sections contain the optical unit-interfacing portions. The optical unit comprises a stainless steel frame having a low coefficient of thermal expansion and a viewing portion which is arranged within the frame and which is made of a glass having a coefficient of thermal expansion not greater than that of the frame. The frame includes the body-interfacing portion of the optical unit. Such a sanitary sight indicator could be incorporated into a production process line as sight flow indicator.

According to another embodiment of the present invention incorporating a Herberts window assembly, the process-interfacing portion of the body is adapted to interface with a tank. In this embodiment, the body preferably comprises an integral part of the tank whereby the process-interfacing portion is actually a transition between the optical-interfacing portion and the remainder of the tank. Such a sanitary sight indicator could be incorporated into a production process as a sight window.

According to still another embodiment of the present invention, the process-interfacing portion of the body is adapted to interface with a tank and the body comprises an integral part of the tank. As such, the process-interfacing portion of the body is actually a transition between the optical unit-interfacing portion and the remainder of the tank. The optical unit of this embodiment is similar in shape to the Herberts window assembly, however, both the viewing portion and the body-interfacing portion of the optical unit are made of a transparent material, such as acrylic or polycarbonate. Such a sanitary sight indicator could incorporated into a production process as a sight window.

These and other features of the invention are fully described and particularly pointed out in the claims. The following description and annexed drawings set forth in detail certain illustrative embodiments, however, these embodiments are indicative of but a few of the various ways in which the principles of the invention may be employed.

BRIEF DESCRIPTION OF THE DRAWINGS

In the annexed drawings:

FIG. 2 is an exploded perspective view of certain components of the sight indicator of Figure these components including a body and an optical unit;

FIG. 3 is a perspective view of an alternate optical unit which may be used in the sanitary sight indicator of FIG. 1;

DETAILED DESCRIPTION

Figure 1:
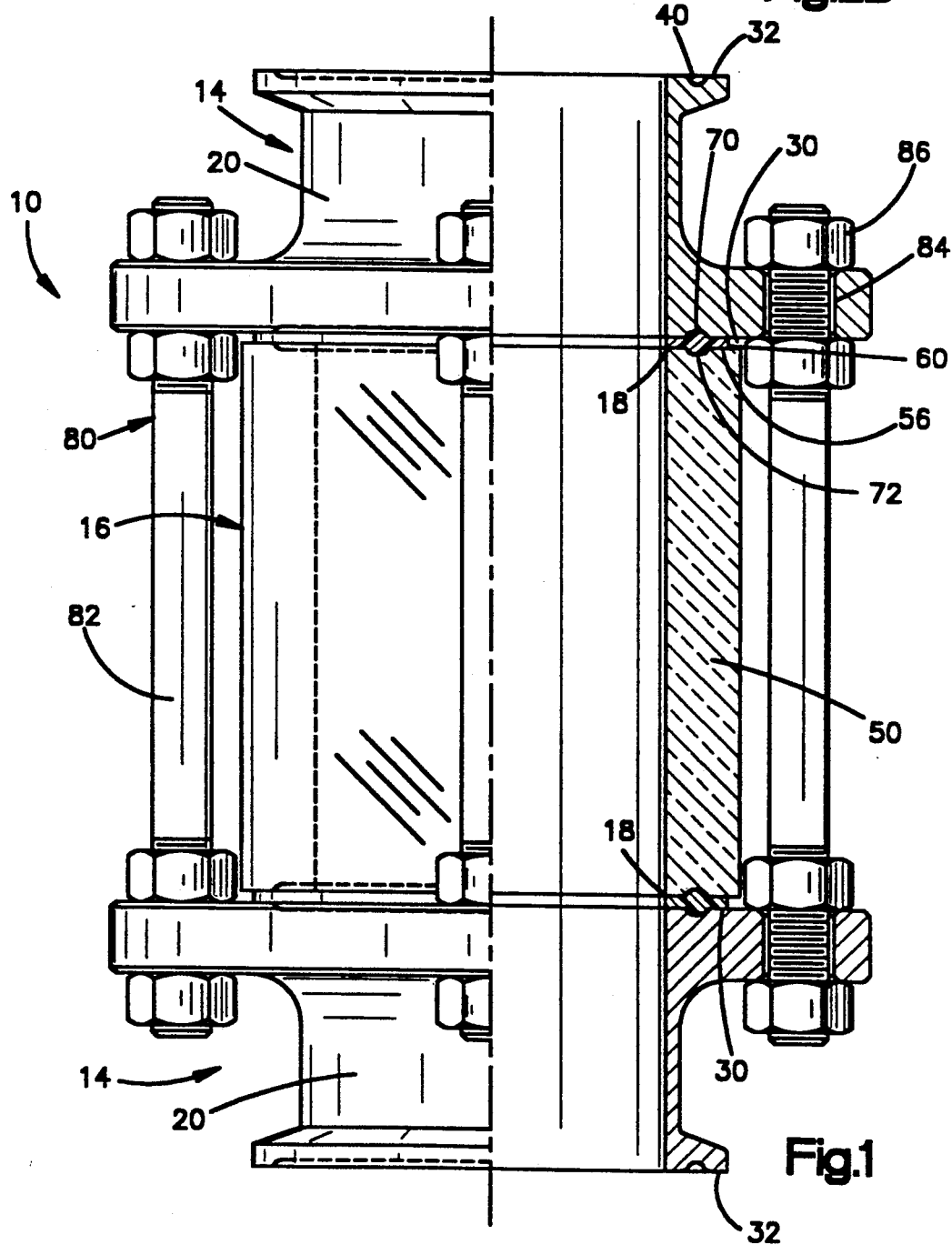
FIG. 1 is side view of a sanitary sight indicator according to one embodiment of the present invention, the left half of the indicator being shown in plan and the right half of the indicator being shown in section.

Referring now to the drawings in detail and initially to FIGS. 1 and 2, a sanitary sight indicator according to the present invention is indicated generally at 10. As is explained in more detail below, the sanitary sight indicator 10 is designed so that it may be incorporated into a process line (not shown) to view the contents flowing therethrough and thus could be specifically referred to as a sight flow indicator. The design of the sanitary sight indicator 10 is believed to be such that leakage into the production process is kept at an extreme minimum and the contents of the production process will not become lodged in the sight indicator. Additionally, the indicator 10 is designed to greatly reduce any tendencies towards failure which would result in contamination of the contents of the production process.

The sanitary sight indicator 10 comprises a body which is indicated generally at 14, an optical unit which is indicated generally at 16, and sanitary connections 18 between the body 14 and the optical unit 16. "Sanitary connection" in this context corresponds to a connection which satisfies generally accepted and approved industry standards, such as those formulated by relevant organizations. Because sanitary connections 18 are employed between the body 14 and the optical unit 16, the sanitary sight indicator 10 may used in production processes having high sanitary standards, such as those used in the production of food, pharmaceutical or cosmetic products.

The body 14 comprises a pair of head members 20 which are made of an approved sanitary material such as 304 stainless steel or 316 stainless steel. The head members 20 are essentially identical and the geometry of these members is best explained by referring to FIGS. 1 and 2. The head members 20 are symmetrically coupled, via the sanitary connections 18, to opposite ends of the optical unit 16. Consequently, the head members 20 may be viewed as having optical unit-interfacing portions 30 which interface with the optical unit 16.

The head members 20 additionally each include a process-interfacing portion 32 which is adapted to interface with the process line. In a typical application, this interface would be a suitable sanitary connection, such as one comprising butt-welds or bevel seat fittings. Alternatively, and as illustrated, the process-interfacing portions 32 may include a sanitary-gasket groove 40 designed to cooperate with a sanitary gasket (not shown) and a corresponding sanitary-gasket groove in the process line. As such the sanitary-gasket groove 40 would possess essentially the same features as the sanitary gasket-grooves discussed below.

The optical unit 16 includes a cylindrical viewing portion 50 for viewing the contents of the production process and two end portions 56 which are co-planar extensions of the viewing portion 50 and which are positioned at opposite ends thereof. The end portions 56 interface with the optical unit-interfacing portions 30 of the body 14 and thus may be referred to as the body-interfacing portions of the optical unit 16. The optical unit 16 is preferably made of a suitable rigid transparent material, such as borosilicate glass, acrylic, or polycarbonate, and more preferably is made of acrylic.

Alternatively, the sanitary sight indicator 10 may include the optical unit 16' shown in FIG. 3. The optical unit 16' includes a cylindrical viewing portion 50' and two end, or body-interfacing, portions 56'. In contrast to the optical unit 16, the body-interfacing portions 56' are not substantially co-planar extensions of the viewing portion 50', but rather are flanged outwardly therefrom. The end portions 56 are preferably molded integral with the viewing portion 50 of the unit 16, rather than cut therefrom. Such integral molding is believed to increase the overall strength of the optical unit 16 and thereby greatly reduce any tendencies towards failure which would result in contamination of the contents of the production process. The optical unit 16' is preferably made of a suitable rigid transparent material, such as borosilicate glass, acrylic, or polycarbonate, and more preferably is made of borosilicate glass.

Figure 2A:
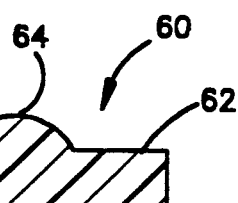
FIG. 2A is an enlarged cross sectional view of a sanitary gasket.

The sanitary connections 18 each includes a sanitary gasket 60, an enlarged cross-sectional view of which is illustrated in FIG. 2A. As shown, the sanitary gasket 60 includes a substantially flat annular portion 62 and annular projections 64 and 66 which are approximately semi-circular in cross-sectional shape and which extend outwardly from opposite surfaces of the annular portion 62. The sanitary gaskets 60 are made of an approved sanitary material such as Buna N, EPDM, Viton, PTFE, Silicone, or Polyethylene.

Each of the sanitary connections 18 further includes a set of corresponding sanitary gasket-grooves 70 and 72 in the body 14 and the optical unit 16, respectively. More particularly, the sanitary gasket-grooves 70 are provided in the optical unit-interfacing portions 30 of the head members 20 and the sanitary gasket-grooves 72 are provided in the body-interfacing portions 56 of the optical unit 16. If the optical unit 16' is used, sanitary gasket-grooves 72' are provided in the body-interfacing portions 56'.

Figure 2B:
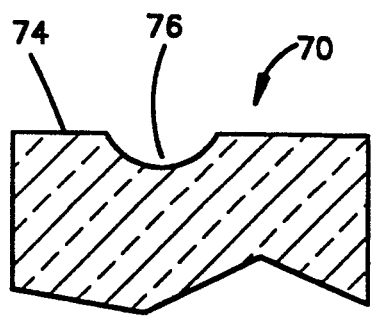
FIG. 2B is an enlarged cross-sectional view of a sanitary- gasket groove.

The features of the sanitary gasket-grooves 70 and 72 are best explained by referring to FIG. 2B which is an enlarged cross-sectional view of the sanitary gasket-groove 70. As shown, the sanitary gasket-groove 70 includes a flat annular portion 74 for supporting the flat annular portion 62 of the stationary gasket and a semi-circular in cross section channel 76 for supporting the projecting portion 64/66 of the stationary gasket 60. It should be noted that although only sanitary gasket-groove 70 is shown in detail, the sanitary gasket-grooves 72/72' will contain analogous features.

When the sanitary sight indicator 10 is assembled, the sanitary gaskets 60 are sandwiched between the respective optical unit-interfacing portions 30 of the head members 20 and the body-interfacing portions 56/56' of the optical unit 16/16'. More particularly, the flat annular portion 62 of the sanitary gasket 60 will be positioned between the flat annular portions 74 of the sanitary-gasket grooves 70 and 72, and the annular projections 64 and 66 of the sanitary gasket 60 will be positioned within the respective channel 76. In this manner, the sanitary connections 18 are established between the body 14 and the optical unit 16/16'.

The body 14 and the optical unit 16/16' are coupled together by a coupling device 80. "Coupling device" in this context corresponds to any device, regardless of whether it is structurally equivalent to the disclosed device, which serves to couple these components together. In the illustrated embodiment, the coupling device 80 comprises a set of threaded studs 82 which are inserted through aligned openings 84 in the head members 20. Nuts 86 are provided to appropriately compress the head members 20 towards each other to create a mechanical connection between 14 and the optical unit 16/16'.

Applicants have developed prototypes of the sanitary flow indicator 10 which incorporate the illustrated geometry and preferred features. In a first prototype, the body 14 was constructed of 304 stainless steel and the optical unit 16 was molded from borosilicate glass and included flanged body-interfacing portions 56. This prototype was tested using conventional methods and equipment, and the testing specifically involved the following sequential steps:

1. pressurizing the indicator to a pressure of 300 psig, holding this pressure for thirty seconds, and then reducing the pressure to 0 psig;
2. pressurizing the indicator to a pressure of 450 psig, holding this pressure for one minute, and then reducing the pressure to 0 psig; and
3. pressurizing the indicator by 50 psig increments until it fails.

When tested in this manner, the optical unit 16, or more particularly the viewing portion 50, failed at approximately 575 psig. Thus the failure point of the indicator 10 was substantially greater than a test pressure of 225 psig, and thus could conservatively be used in a production process having a maximum working pressure of 150 psig. When these testing methods were repeated on an essentially identical unit, the optical unit 16 failed at 600 psig in a similar manner.

In a second prototype, the body 14 was also constructed of 304 stainless steel, however, the optical unit 16' was made of acrylic and included co-planar body-interfacing portions 56'. The testing of this prototype consisted of the following sequential steps:

1. pressurizing the indicator to a pressure of 300 psig, holding this pressure for thirty seconds, and then reducing the pressure to 0 psig;
2. pressurizing the indicator to a pressure of 450 psig, holding this pressure for one minute, and then reducing the pressure to 0 psig;
3. pressurizing the indicator to a pressure of 600 psig, holding this pressure for one minute, and then reducing the pressure to 0 psig; and
4. pressurizing the indicator by 50 psig increments until it fails.

When tested in this manner, the stationary gasket 60 slipped out of the indicator at approximately 900 psig, and thus this indicator also demonstrated a failure point which was substantially greater than a test pressure of 225 psig. Consequently, this indicator could conservatively be used in a production process having a maximum working pressure of 150 psig. When these testing methods were repeated on an essentially identical indicator, the stationary gasket 60 again slipped out at approximately 900 psig.

Figure 4:
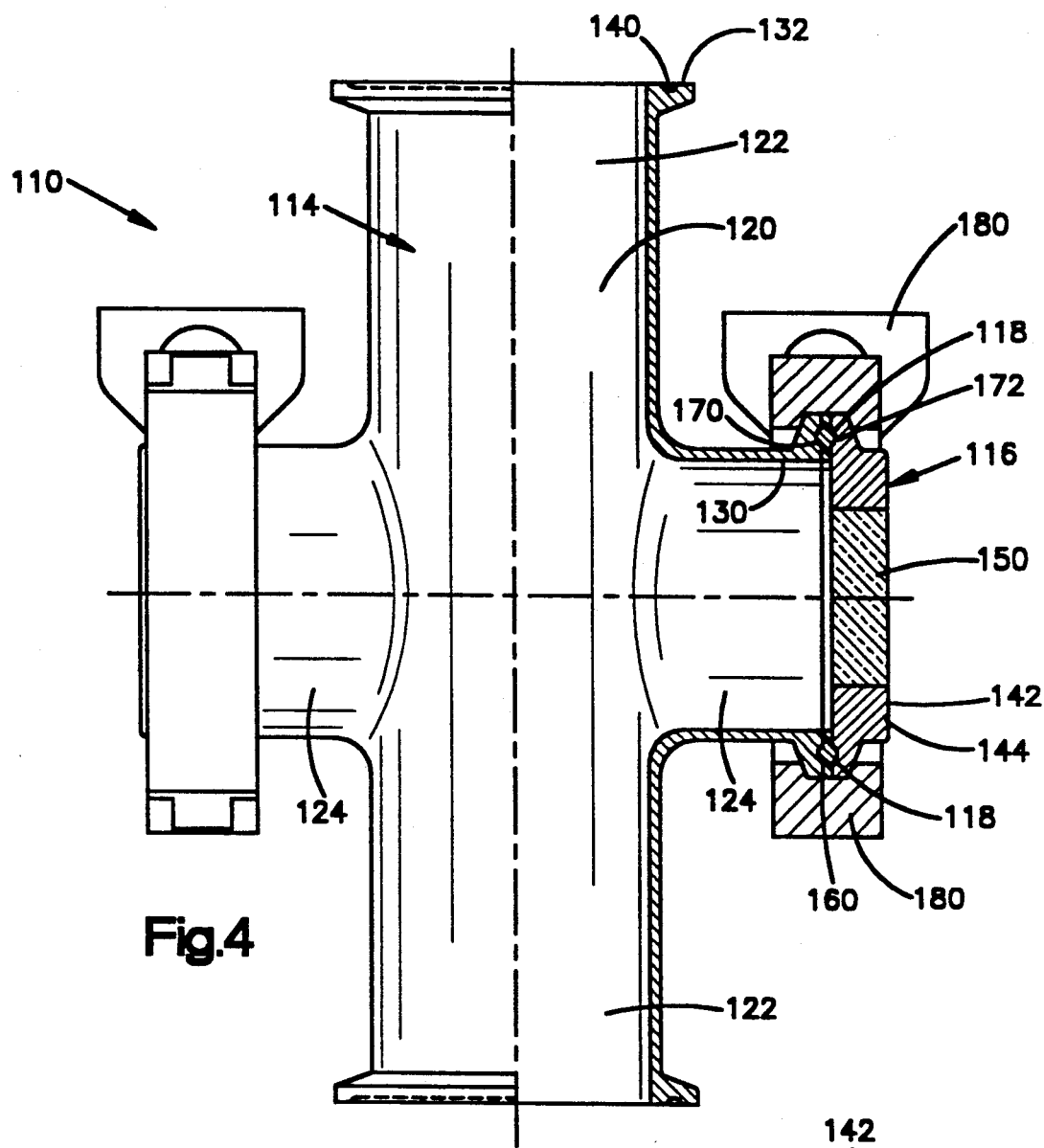
FIG. 4 is a side view of a sanitary sight indicator according to another embodiment of the present invention, the left half of the indicator being shown in plan and the right half of the indicator being shown in section.
Figure 5:
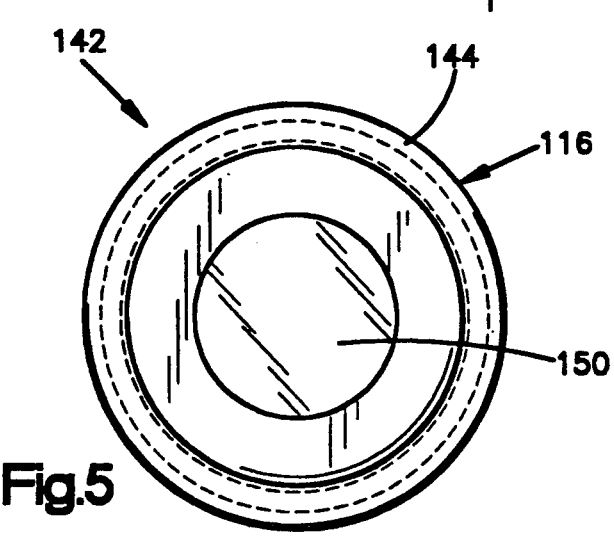
FIG. 5 is a front view of a component of the indicator of FIG. 3, namely an optical unit.
Figure 6:
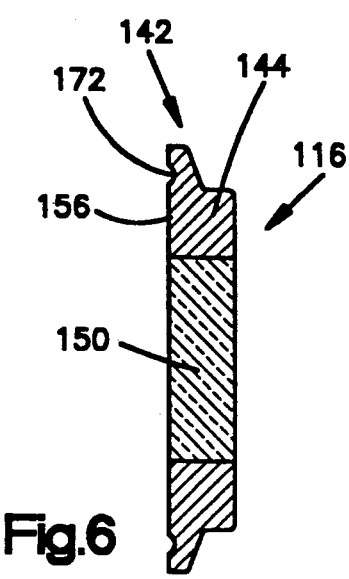
FIG. 6 is a side cross-sectional view of the optical unit of FIG. 5.

Turning now to FIGS. 4-6, another sanitary sight indicator according to the present invention is indicated generally at 110. The sanitary sight indicator 110 is also designed so that it may be incorporated into a process line (not shown) to view the contents flowing therethrough and consequently could be specifically referred to as a sight flow indicator.

The sanitary sight indicator 110 comprises a body which is indicated generally at 114, and at least one, and in the illustrated embodiment two, optical units which are indicated generally at 116. Sanitary connections 118 are made between the body 114 and the optical units 116. In the illustrated embodiment, the body 114 comprises a cross member 120 which is made of an approved sanitary material such as 304 stainless steel or 316 stainless steel. However, other constructions of the body 114 are possible with, and contemplated by, the present invention. For example, the cross member 120 could be replaced with a T-member whereby only one optical unit 116 would be included in the indicator.

The cross member 120 is comprised of two aligned through-flow sections 122 and two aligned transverse sections 124. Each of the transverse sections 124 is coupled, via one of the sanitary connections 118, to one of the optical units 116 Consequently, each of the transverse sections 124 may be viewed as having an optical unit-interfacing portion 130.

The through-flow sections 122 each include a process-interfacing portion 132 which is adapted to interface with the process line. In a typical application, this interface will be a suitable sanitary connection, such as one comprising sanitary clamping, butt-welds or bevel seat fittings. When using sanitary clamping as illustrated, the process-interfacing portions 132 may each contain a stationary gasket-groove 140 which possess the same features, and serves the same function, as the sanitary gasket-grooves 76, 70 and 72 discussed above.

Each of the optical units 116 preferably comprises a window assembly 142 which is of the type disclosed in U.S. Pat. No. 4,961,628 to Herberts, the entire disclosure of which is hereby incorporated by reference. Such a window assembly is believed to be extremely resistant even under high pressure and thermal influences. As such, the window assembly 142 serves to greatly reduce any tendencies towards failure which would result in contamination of the contents of the production process.

Each window assembly 142 includes a cylindrical metal frame 144 in which is arranged a transparent insert, or viewing portion, 150 for viewing the contents of the production process. The frame 144 is made of a stainless steel having a low coefficient of thermal expansion and the viewing portion 150 is made of a glass, preferably borosilicate, having a similar or still smaller coefficient of expansion. The frame 144 includes a body-interfacing portion 156 which interfaces with the respective optical unit-interfacing portion 130 of the body 114.

Figure 9:
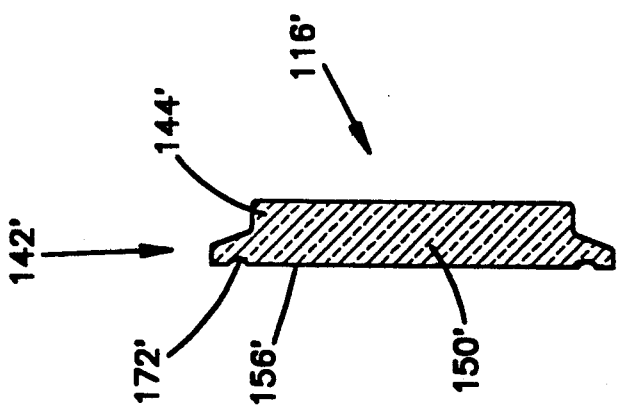
FIG. 9 is a side cross-sectional view of an optical unit similar to that shown in FIG. 6 except that it is completely made of a transparent material.

Alternatively, indicator 110 could incorporate the optical unit 116' shown in FIG. 9. The optical unit 116' comprises a window assembly 142' which is similar in shape to the window assembly 142, however, it is completely made of a transparent plastic material such as acrylic or polycarbonate. The viewing portion 150' of the optical unit 116' comprises the central region of the window assembly 142 while the body-interfacing portion 156' comprises the circumferential border therearound.

The sanitary connections 118 each include a sanitary gasket 160 which is essentially identical to the sanitary gaskets discussed above. Consequently, the sanitary gaskets 160 each include a substantially flat annular portion and annular projections which are approximately semi-circular in cross-sectional shape and which extend outwardly from opposite surfaces of the flat annular portion. These portions of the sanitary gasket 160 are shown, but not specifically numbered, in the drawings.

Each of the sanitary connections 118 further includes a set of corresponding sanitary-gasket grooves 170 and 172 in the body 114 and the optical units 116, respectively. More particularly, the sanitary gasket-grooves 170 are provided in the optical unit-interfacing portions 130 of the transverse sections 124 and the sanitary gasket-grooves 172 are provided in the body-interfacing portions 156 of the frame 144. The sanitary gasket-grooves 170 and 172 are preferably essentially identical to the sanitary gasket-grooves 70 and 72 discussed above.

When the sanitary sight indicator 110 is assembled, the sanitary gaskets 160 are sandwiched between the respective optical unit-interfacing portions 130 of the transverse sections 124 and the body-interfacing portions 156 of the optical unit 116. More particularly, the flat annular portion of the sanitary gasket 160 will be positioned between the flat annular portions of the sanitary-gasket grooves 170 and 172, and the annular projections of the sanitary gasket 160 will be positioned within the channels of the sanitary-gasket grooves. In this manner, the sanitary connections 118 are established between the body 114 and the optical unit 116.

The body 114 and the optical unit 116 are coupled together by a coupling device 180. "Coupling device" in this context corresponds to any device, regardless of whether it is structurally equivalent to the disclosed device, which serves to couple these components together. In the illustrated embodiment, the coupling device 180 comprises a three-sectioned clamp 182 for each optical unit 116, such as the widely used TRI-CLAMP ®.

Figure 8:
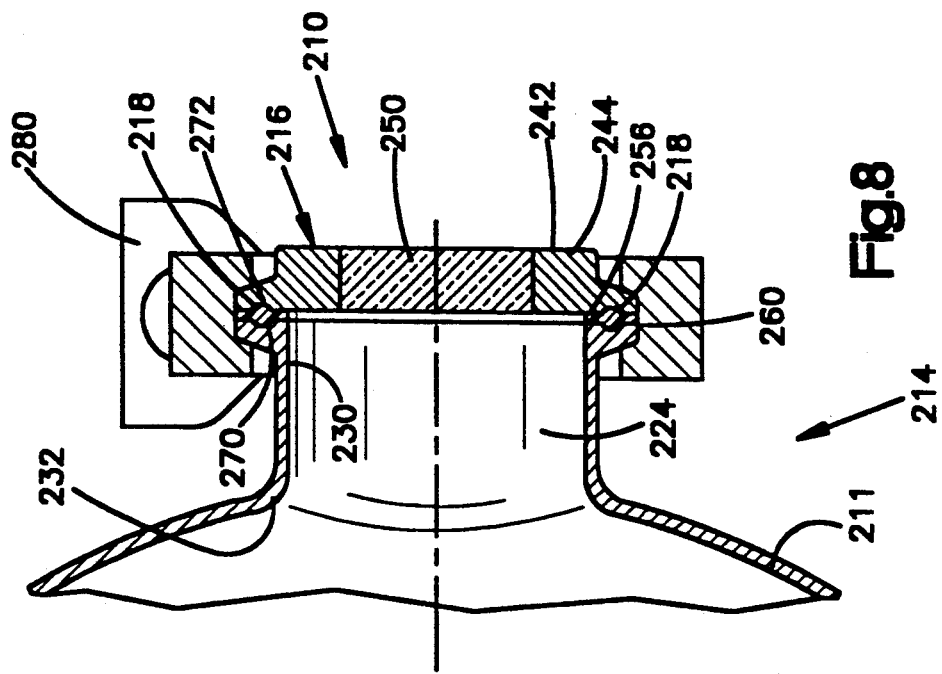
FIG. 8 is an enlarged side view of the sight indicator of FIG. 7.
Figure 7:
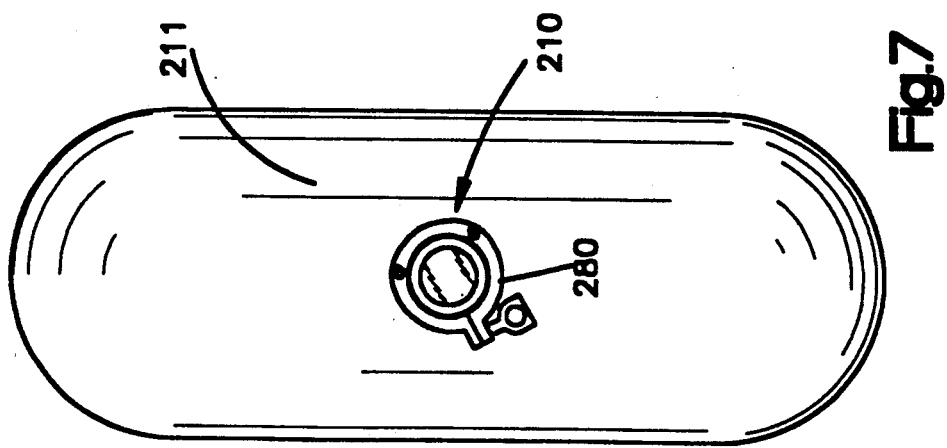
FIG. 7 is a front view of a sight indicator according to another embodiment of the present invention, the sight indicator being shown installed on a process tank.

Referring now additionally to FIGS. 7 and 8, another sanitary sight indicator according to the present invention is indicated generally 210. The sanitary sight indicator 210 is designed to be installed on a process tank 211 and thus may be specifically referred to as a sight window.

The sanitary sight indicator 210 comprises a body which is indicated generally at 214 and an optical unit which is indicated generally at 216. The body 214 includes an optical unit-interfacing portion 230 which interfaces with the optical unit 216 and a process-interfacing portion 232 which is adapted to interface with the production process. In the illustrated embodiment, the body 214 comprises an integral part of the process tank 211 and thus the process-interfacing portion 232 comprises a transition between the optical unit-interfacing portion 230 and the remainder of the tank 211.

Each of the optical units 216 preferably comprises a window assembly 242 which is of the type disclosed in U.S. Pat. No 4,961,628 to Herberts, the entire disclosure of which has already been incorporated by reference. Consequently, the window assembly 242 is essentially identical to the window assembly 142 discussed above, and includes a cylindrical metal frame 244 in which is arranged a transparent insert, or viewing portion, 250, for viewing the contents of the process tank 211. The frame 244 includes a body-interfacing portion 256 which interfaces with the optical unit-interfacing portion 230 of the body 214. Alternatively, the indicator 210 could incorporate the optical unit 116' shown in FIG. 9.

The sanitary connection 218 includes a sanitary gasket 260 which is essentially identical to the sanitary gaskets discussed above. The sanitary connection 218 further includes a set of corresponding sanitary-gasket grooves 270 and 272 in the body 214 and the optical unit 216, respectively. More particularly, the sanitary gasket-groove 270 is provided in the optical unit-interfacing portion 230 of the body 214 and the sanitary gasket-groove 272 is provided in the body-interfacing portion 256 of the frame 244. The sanitary gasket-grooves 270 and 272 are preferably essentially identical to the sanitary gasket-grooves discussed above.

When the sanitary sight indicator 210 is assembled, the sanitary gasket 260 is sandwiched between the respective optical unit-interfacing portion 230 of the body 214 and the body-interfacing portions 256 of the optical unit 216. More particularly, the flat annular portion of the sanitary gasket 260 will be positioned between the flat annular portions of the sanitary-gasket grooves 270 and 272, and the annular projections of the sanitary gasket 260 will be positioned within the channels of the sanitary-gasket grooves. In this manner, the sanitary connection 218 is established between the body 214 and the optical unit 216. The body 214 and the optical unit 216 are coupled together by a coupling device 280, which may be essentially the same as the coupling device 180 discussed above.

A prototype was developed by applicants which incorporated the illustrated geometry and the preferred features of the sanitary sight indicator 210. The testing of this prototype consisted of the following sequential steps:

1. pressurizing the indicator to a pressure of 150 psig, holding this pressure for thirty seconds, and then reducing the pressure to 0 psig;
2. pressurizing the indicator to a pressure of 300 psig, holding this pressure for thirty seconds, and then reducing the pressure to 0 psig;
3. pressurizing the indicator to a pressure of 450 psig, holding this pressure for thirty seconds, then reducing the pressure to 0 psig;
4. pressurizing the indicator to a pressure of 600 psig, holding this pressure for one minute, and then reducing the pressure to 0 psig;
5. pressurizing the indicator to a pressure of 900 psig, holding this pressure for one minute, and then reducing the pressure to 0 psig;
6. pressurizing the indicator to a pressure of 1200 psig, holding this pressure for one minute, and then reducing the pressure to 0 psig; and
7. pressurizing the indicator until it fails.

When tested in this manner, the stationary gasket 260 slipped out of the indicator at approximately 1480 psig. Consequently, the pressure rating of the sight indicator 210 greatly exceeds the typical industry-required test pressure rating of 225 psig for production processes having a maximum working pressure of 150 psig.

One may now appreciate that the present invention provides a sanitary sight indicator which includes a sanitary connection between the body and the optical unit. In this manner, leakage into the production process is kept at an extreme minimum and the opportunity for the contents of the production process to become lodged in the sight indicator is minimized to industry accepted levels. Additionally, the viewing portion of the optical unit is designed to greatly reduce any tendencies towards failure.

Although the invention has been shown and described with respect to certain preferred embodiments, it is obvious that equivalent alterations and modifications will occur to others skilled in the art upon the reading and understanding of this specification. The present invention includes all such equivalent alterations and modifications and is limited only by the scope of the following claims.

What is claimed is:

1. A sanitary tubular sight indicator for viewing the contents of a production process, said indicator comprising a body having first and second head members, an elongated optical unit, a sanitary connection between said first head member and said optical unit, and a coupling device for connecting said body and said optical unit together;

said first head member including a first process-interfacing portion which is adapted to interface with the production process and a first optical-interfacing portion which interfaces with said optical unit;

said optical unit including a viewing portion for viewing the contents of the production process and a first body-interfacing portion which interfaces with said first optical-interfacing portion of said first head member;

said sanitary connection including a sanitary gasket including a substantially flat annular portion, and first and second annular projections which are essentially semi-circular in cross-sectional shape and which extend outwardly from opposite sides of said annular portion;

said sanitary connection further including a sanitary gasket-groove in each of said first optical unit-interfacing portion and said first body-interfacing portion, each of said sanitary gasket-grooves including a flat surface supporting said flat annular portion of said sanitary gasket and a channel supporting one of said first and second annular projections of said sanitary gasket;

wherein said first process-interfacing portion of said first head member is adapted to interface with a process line.

2. A sanitary tubular sight indicator as set forth in claim 1 further comprising a second sanitary connection between said second head member and said optical unit;

said second head member including a second process-interfacing portion which is adapted to interface with the production process and a second optical-interfacing portion which interfaces with said optical unit;

said optical unit including a second body-interfacing portion which interfaces with said second optical-interfacing portion of said second head member;

said second sanitary connection including a second sanitary gasket including a substantially flat annular portion, and first and second annular projections which are essentially semi-circular in cross-sectional shape and which extend outwardly from opposite sides of said annular portion;

said second sanitary connection further including a second sanitary gasket-groove in each of said second optical unit-interfacing portion and said second body-interfacing portion, each of said sanitary gasket-grooves including a flat surface supporting said flat annular portion of said sanitary gasket and a channel supporting one of said first and second annular projections of said sanitary gasket;

wherein said second process-interfacing portion of said second head member is adapted to interface with the process line.

3. A sanitary sight indicator as set forth in claim 2 wherein said viewing portion of said optical unit is cylindrical in shape and has an axial dimension greater than its radial dimension.

4. A sanitary sight indicator as set forth in claim 3 wherein said body-interfacing portions of said optical unit comprise flanged end portions positioned at opposite ends of said viewing portion.

5. A sanitary sight indicator as set forth in claim 4 wherein said optical unit is made of borosilicate glass and wherein said flanged end portions are integrally molded with said viewing portion.

6. A sanitary sight indicator as set forth in claim 3 wherein said optical unit is made of a rigid transparent material.

7. A sanitary sight flow indicator as set forth in claim 6 wherein said optical unit is made of a material selected from a group consisting of borosilicate glass, acrylic, and polycarbonate.

8. A sanitary sight indicator as set forth in claim 6 wherein said body-interfacing portions of said optical unit comprise substantially co-planar extensions of said viewing portion.

9. A sanitary sight indicator as set forth in claim 6 wherein said body comprises a pair of head members which are essentially identical and which each include a process-interfacing portion and an optical unit-interfacing portion.

10. A sanitary sight indicator as set forth in claim 9 wherein said body is made of stainless steel.

11. A sanitary sight indicator as set forth in claim 1 wherein said sanitary gasket is made of an approved sanitary gasket material.

12. A sanitary sight indicator as set forth in claim 1 wherein said sanitary gasket is made of a material selected from the group consisting of Buna N, EPDM, Viton, PTFE, Silicone, and Polyethylene.

13. A sanitary sight indicator as set forth in claim 1 wherein said optical unit comprises a window assembly including a frame which is made of a stainless steel of low coefficient of thermal expansion and a transparent insert which is arranged within said frame and which is made of a glass having a coefficient of thermal expansion not greater than that of said frame.

14. A sanitary sight indicator as set forth in claim 1 wherein said optical unit comprises a window assembly made of a transparent plastic material, said window assembly including a central region which forms said viewing portion and a circumferential border therearound which includes said body-interfacing portion.

15. A sanitary sight indicator as set forth in any of claims 2-10, 13, or 14 wherein said sanitary gasket is made of an approved sanitary gasket material.

16. A sanitary sight indicator as set forth in any of claims 2-14 10, 13, or 14 wherein said sanitary gasket is made of a material selected from the group consisting of Buna N, EPDM, Viton, PTFE, Silicone, and Polyethylene.

* * * * *